US010682376B2

(12) United States Patent
Weibel et al.

(10) Patent No.: US 10,682,376 B2
(45) Date of Patent: *Jun. 16, 2020

(54) PHARMACEUTICAL COMPOSITIONS

(71) Applicant: VIFOR FRESENIUS MEDICAL CARE RENAL PHARMA LTD., St. Gallen (CH)

(72) Inventors: Ludwig Daniel Weibel, Waldstatt (CH); Erik Philipp, Arbon (CH)

(73) Assignee: Vifor Fresenius Medical Care Renal Pharma Ltd, St. Gallen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/170,650

(22) Filed: Oct. 25, 2018

(65) Prior Publication Data

US 2019/0117686 A1 Apr. 25, 2019

Related U.S. Application Data

(63) Continuation of application No. 15/389,549, filed on Dec. 23, 2016, which is a continuation of application No. 12/743,120, filed as application No. PCT/EP2008/065444 on Nov. 13, 2008, now Pat. No. 9,561,251.

(30) Foreign Application Priority Data

Nov. 16, 2007 (EP) .................................... 07120837

(51) Int. Cl.
| | | |
|---|---|---|
| A61K 33/26 | (2006.01) | |
| A61K 9/00 | (2006.01) | |
| A61K 9/16 | (2006.01) | |
| A61K 9/20 | (2006.01) | |
| A61K 47/02 | (2006.01) | |

(52) U.S. Cl.
CPC .............. *A61K 33/26* (2013.01); *A61K 9/009* (2013.01); *A61K 9/0053* (2013.01); *A61K 9/0056* (2013.01); *A61K 9/1623* (2013.01); *A61K 9/1635* (2013.01); *A61K 9/1652* (2013.01); *A61K 9/205* (2013.01); *A61K 9/2018* (2013.01); *A61K 9/2027* (2013.01); *A61K 9/2059* (2013.01); *A61K 9/2095* (2013.01); *A61K 47/02* (2013.01)

(58) Field of Classification Search
CPC .............. A61K 2300/00; A61K 9/0053; A61K 9/2027; A61K 9/1652; A61K 47/02; A61K 9/0065; A61K 9/2031; A61K 9/2072; A61K 9/209; A61K 9/0056; A61K 9/009; A61K 9/1623; A61K 9/1635; A61K 9/2018; A61K 9/205; A61K 9/2059; A61K 9/2095

See application file for complete search history.

(56) References Cited

U.S. PATENT DOCUMENTS

| | | | |
|---|---|---|---|
| 2,820,740 | A | 1/1958 | London et al. |
| 3,076,798 | A | 2/1963 | Mueller et al. |
| 3,499,837 | A | 3/1970 | Jaumarajs |
| 3,574,184 | A | 4/1971 | Aslop et al. |
| 3,591,616 | A | 7/1971 | Baldt |
| 3,928,581 | A | 12/1975 | Dahlberg et al. |
| 4,181,718 | A | 1/1980 | Mason et al. |
| 4,327,076 | A | 4/1982 | Puglia et al. |
| 4,474,859 | A | 10/1984 | Watanabe |
| 4,581,141 | A | 4/1986 | Ash |
| 4,668,400 | A | 5/1987 | Veech |
| 4,749,695 | A | 6/1988 | Schwengers |
| 4,788,281 | A | 11/1988 | Tosoni |
| 4,869,828 | A | 9/1989 | Hoots et al. |
| 4,970,079 | A | 11/1990 | Hem et al. |
| 5,213,692 | A | 5/1993 | Hjersted |
| 5,248,492 | A | 9/1993 | Groman et al. |
| 5,496,545 | A | 5/1996 | Holmes-Farley et al. |
| 5,514,281 | A | 5/1996 | Boos et al. |
| 5,531,922 | A | 7/1996 | Okinaka et al. |
| 5,624,668 | A | 4/1997 | Lawrence et al. |
| 5,633,006 | A | 5/1997 | Catania et al. |
| 5,667,775 | A | 9/1997 | Holmes-Farley et al. |
| 6,103,126 | A | 8/2000 | Boos et al. |
| 6,117,451 | A | 9/2000 | Kumar |
| 6,143,324 | A * | 11/2000 | Michaud ............... A61K 9/2059 424/452 |
| 6,156,332 | A | 12/2000 | Bakal et al. |
| 6,174,442 | B1 * | 1/2001 | Geisser .................. A61K 33/26 210/645 |
| 6,475,510 | B1 | 11/2002 | Venkatesh et al. |

(Continued)

FOREIGN PATENT DOCUMENTS

| | | |
|---|---|---|
| AU | 2013203333 B2 | 5/2013 |
| CA | 2571364 A1 | 12/2006 |

(Continued)

OTHER PUBLICATIONS

Banker, G.S. et al., Tablet Formulation and Design Book, 1980, pp. 61-107, vol. 1, United States of America.
Crosby, S.A. et al., Kinetics of Phosphate Adsorption by Iron Oxyhydroxides in Aqueous Systems, Estuarine, Coastal and Shelf Science col. 19, Dec. 1, 1983, pp. 257-270.
Daichuan, Dong et al., Preparation of Uniform β-FeO(OH) Colloidal Particles By Hydrolysis Of Ferric Salts Under Microwave Irradiation, Materials Research Bulletin vol. 30, No. 5, Oct. 2, 1994, pp. 537-541, vol. 30 No. 5, USA.
Dousma, J. et al., The Influence of Chloride Ions on the Formation of Iron (III) Oxyhydroxide, J. inorg. nucl. Chem. Dec. 27, 1977, pp. 1089-1093, vol. 40, Printed in Great Britain.

(Continued)

*Primary Examiner* — Johann R Richter
*Assistant Examiner* — Danielle Sullivan
(74) *Attorney, Agent, or Firm* — Finnegan, Henderson, Farabow, Garrett & Dunner LLP

(57) ABSTRACT

Pharmaceutical compositions for oral administration, in particular administration as an oral delivery system to be swallowed directly or capable of disintegration in the oral cavity, comprising iron oxy-hydroxide in high loading.

65 Claims, No Drawings

(56) References Cited

U.S. PATENT DOCUMENTS

| | | | |
|---|---|---|---|
| 6,521,247 B1* | 2/2003 | deVries | A23L 33/15 424/439 |
| 6,576,665 B2 | 6/2003 | Dennett, Jr. et al. | |
| 6,764,997 B2 | 7/2004 | Tenengauzer et al. | |
| 6,875,445 B2 | 4/2005 | Dennett, Jr. et al. | |
| 6,903,235 B2 | 6/2005 | Hsiao et al. | |
| 7,465,465 B2 | 12/2008 | Haslam et al. | |
| 9,561,251 B2* | 2/2017 | Weibel | A61K 9/1623 |
| 2002/0044969 A1 | 4/2002 | Harden | |
| 2008/0107787 A1 | 5/2008 | Prakash et al. | |
| 2008/0145410 A1 | 6/2008 | Ambuhl et al. | |
| 2009/0169645 A1 | 7/2009 | Muller et al. | |
| 2009/0317459 A1 | 12/2009 | Pennel et al. | |
| 2017/0143634 A1 | 5/2017 | Chofflon et al. | |

FOREIGN PATENT DOCUMENTS

| | | |
|---|---|---|
| DE | 19547356 A1 | 12/2006 |
| EP | 068125 B1 | 12/1996 |
| EP | 1757299 A1 | 8/2005 |
| EP | 1757299 | 2/2007 |
| EP | 1932808 A1 | 5/2007 |
| EP | 1932807 A1 | 6/2008 |
| GB | 918929 A | 2/1963 |
| GB | 1249558 A | 10/1971 |
| WO | 92/01458 | 2/1992 |
| WO | 9201458 A1 | 2/1992 |
| WO | WO97/22266 | 6/1997 |
| WO | 200213793 A2 | 2/2002 |
| WO | 03/086321 | 10/2003 |
| WO | 2005018651 A1 | 3/2005 |
| WO | 2006/000547 | 1/2006 |
| WO | 2006000547 A2 | 1/2006 |
| WO | 2010015827 A2 | 8/2008 |
| WO | 2009062993 A1 | 5/2009 |
| WO | 2015078900 A1 | 6/2015 |

OTHER PUBLICATIONS

WAde, Ainley, and Paul J. Weller., Handbook of Pharmaceutical Excipients., 1994, pp. 483-488, Second Edition, American Pharmaceutical association, Washington.
Schwertmaixn, U., Cornell, R. M., Iron Oxides in the Laboratory, Mar. 1991, pp. 1-100, Wiley-VCH.
Jing, Shi-Bing, Chemistry Express, Journal, 1992, pp. 93-96, vol. 7 No. 1, Japan.
Langmuir, D., Variations in the Stability of Precipitated Ferric Oxyhydroxides, Nonequilibrium Systems in Natural Waters, Jun. 1, 1971, pp. 209-234, Los Angeles.
Melikhov, I.V. et al., Kinetics of Hydroxide Fe(III) Solid Phase Formation, Journal of Colliod and Interface Science, May 1987, pp. 1-9, vol. 117, No. 1, Moscow.
Mitra, N.K. et al., Physico-Chemical Characteristics of Same Synthetic Hydroxide Hydrogels, Indian Ceramics, Feb. 1985, pp. 215-218, vol. 27. No. 11, Calcutta.
Pope, W., A Comparison of Various Forms of Colloidal Ferric Hydroxide, Journal, 1924, pp. 233-235, Cambridge.
King, Robert E., Tablets, Capsules and Pills, Remington Pharmaceutical Science, 1980, pp. 1553-1576, 16th Edition, Philadelphia.
Sheth, B. B. et al., Compressed Tablets, Pharmaceutical Dosage Forms, 1980, pp. 109-185, vol. 1, New York.
Shigetomi, Y. et al., The Adsorption Behaviors of Several Phosphate Ions on Composite Adsorbent made of Hydrous Fe(III) Oxide and Polyacrylamide, J. inorg. nucl. Chem. 1981, pp. 2129-2131, vol. 43, Pergamon Press Ltd, Great Britian.
Spengler, K. et al., Characterization and Extracorporeal Application of a New Phosphate Binding Agent, Eur. J. Clin. Chem. Clin, Biochem.1994, pp. 733-739, vol. 32, New York.
Thole, S. et al., Effects of Wafer Composition on Adsorption of Phosphate on Iron Oxyhydroxide Sludges, Vom Wasser vol. 77, 1992, pp. 313-321, Berlin.

Mohan Shailender, Compression Physics of Pharmaceutical Powders: A Review, IJPSR 2012, pp. 1580-1592, vol. 3, No. 6, India.
Leane, Michael. et al., A proposal for a drug product Manufacturing Classification System (MCS) for oral solid dosage forms, Pharm Dev Technol 2014, pp. 1-10, United Kingdom.
Mccormick; Douglas, Evolutions in Direct Compression, Pharmaceutical Technology, 2005, pp. 52-62.
Covic, Adrian. et al., Hyperphosphatemia in patients with ESRD: assessing the current evidence linking outcomes with treatment adherence, BMC Nephrology vol. 14, No. 153,, 2013, pp. 1-9.
Coyne, Daniel W. et al., Real-world effectiveness of sucroferric oxyhydroxide in patients on chronic hemodialysis: A retrospective analysis of pharmacy data, Clinical Nephrology 2017, pp. 1-9, USA.
Geisser, P. et al., PA21: a novel phosphate binder for the treatment of hyperphosphatemia in chronic kidney disease, Clinical Nephrology 2010, pp. 4-11, vol. 74, Switzerland.
Voigt, Von Rudolf. et al., Pharmazeutischie technologie, 2000, pp. 163-164.
Proscribing Information for Auryxia, Keryx BioPharmaceuticals, New york.
Proscribing Information for VELPHORO, Fresenius Medical Care North America, Massachusetts.
Wang, Steven. et al., Serum phosphorus levels and pill burden are inversely associated with adherence in patients on hemodialysis, Nephrol Dial Transplant 2013, pp. 1-9, Denver.
Wuthrich, Rudolf P. et al., Randomized Clinical Trial of the Iron-Based Phosphate Binder PA21 in Hemodialysis Patients, Clin J Am Soc Nephrol 8, 2013, pp. 280-289, Switzerland.
King, Jim., New Phosphate Binder for Renal Failure Lowers Pill Burden, 2013, pp. 1-2, Medscape Medical News, Turkey.
Carroll, John., Keryx ($KERX) claims a front-line victory with PhIII Zerenex data, 2010, pp. 1, FierceBiotech, Massachusetts.
Chiu, Yi-Wen, et al., Pill Burden, Adherence, Hyperphosphatemia, and Quality of Life in Maintenance Dialysis Patients, Clin J Am Soc Nephrol 4, 2009, pp. 1089-1096, cjasn, Torrance.
Li, Zhe. et al., Direct compaction: An update of materials, troubleshooting, and application, International Journal of Pharmaceutics 529, 2017, pp. 543-556, Elsevier, Shanghai.
Gohel, M. C., et al., A review of co-processed directly compressible excipients, 2005, pp. 76-93, J Pharm Pharmaceut Sci 8(1), India.
Notice of Opposition to European Patent No. EP2222285 dated Sep. 28, 2017.
Goto, Kenta., et al., Pharmaceuticil Evaluation of Multipurpose Excipients for Direct Compressed Tablet Manufacture: Comparisons of the Capabilities of Multipurpose Excipients with Those in General Use, Drug Development and Industrial Pharmacy 25 (8),1999, pp. 869-878. Taylor & Francis. England.
Wade, Ainley, and Paul J. Weller., Handbook of Pharmaceutical Excipients., 1994, pp. 3-4, 21-23, 415-417, 483-488, 500-505, Second Endition, American Pharmaceutical association, Washington.
Introduction to tableting by direct compression, DFE Pharma, Germany.
Joneja S.K., et al., Investigating the Fundamental Effects of Binders on Pharmaceutical Tablet Performance, Drug Development and Industrial Pharmacy 25 (10),1999, pp. 1129-1135, Taylor & Francis, England.
Kornblum, Saul S., Sustained-Action Tablets Prepaired by Employing a Spray-Drying Technique for Granulation, 1969, pp. 125-127, vol. 58, No. 1, Technical Articles, Hoboken.
Thoorens, Gregory. et al., Microcrystalline cellulose, a direct compression binder in a quality by design environment—A review, International Journal of Pharmaceutics 473, 2014, pp. 64-72, Elsevier B.V., Belgium.
Bellinghieri, Guido et al., Emerging Drigs for Hyperphosphatemia, Expert Opin. Emerging Drugs 12(3), 2007, pp. 355-365, Italy.
Fosrenol, Shire US Inc., Wayne, Pa., Oct. 2004.
Lim, "Spherical Composite Particles of Rice Starch and Microcrystalline Cellulose: A New Coprocessed Excipient for Direct Compression," AAPS PharmSciTech 5(2), 2004, pp. 1-10, Bangkok.
Zheng, Polymers in Pharmaceuticals, textbook series for 21st century, Beijing, China Medical Science and technology Press, 1st edition, Aug. 2000, pp. 86-87.

(56) References Cited

OTHER PUBLICATIONS

Second EPO Opposition Filed on Dec. 6, 2014.
Willhelm, Maria. et al., The iron-based phosphate binder PA21 has potent phosphate binding capacity and minimal iron release across a physiological pH range in vitro, Clinical Nephrology, 2014, pp. 251-258, vol. 81, Switzerland.
Yajima et al., Optimization of Size Distribution of Granules for Tablet Compression, Chem. Pharm. Bull.1996, pp. 1056-1060, vol. 44, Toshio Pharmaceutical Inc., Japan.
Third Party Observation filed Feb. 14, 2018 in counterpart European Appln. No. 1403118.0.
Assessment Report, Velphoro European Medicines Agency, Jun. 26, 2014, pp. 1-16.
Hergesell Olaf, et al. Stabilized Polynuclear Iran Hydroxide is an Efficient Oral Phosphate Binder in Uraemic Patients, Nephrol Dial transplant 14, 1999, pp. 863-867.
Shangraw, "Compressed Tablets by Direct Compression," Pharmaceutical Dosage Forms, Tablets, vol. 1, (Herbert A. Lieberman et al) 1989, pp. 196-246.
Handbook of Pharmaceutical Excipients 1986, pp. 289-297.
PhosLo Capsules, Braintree Labratories, Inc., Braintree Mass.
Renagel Tablets, Genzyme Corporation, Cambridge Massachusetts, Oct. 2004.
Kettler et al, "Management of hyperphosphataemia in chronic kidney diseases—challenges and solutions," Clinical Kidney J (2013) 6: 128-136.
Aulton, M.E., "Pharmaceutics, The Science of Dosage Form Design," Second Edition (2002), pp. 404-410, 412, 441 and 459.
Albaaj et al, "Hyperphosphataemia in Renal Failure: Causes, Consequences and Current Management," Drugs: 2003, vol. 63, issue No. 6, pp. 577-596.
Geisser and Philipp, "PA21: a novel phosphate binder for the treatment of hyperphosphatemia in chronic kidney disease," Clinical Nephrology vol. 74, No. 1, Jul. 2010, pp. 4-11.
http://www.anemia.org/professionals/feature-articles/content.ph.pdf, Nov. 6, 2008.
Vifor PA21 clinical_study-results, Jul. 9, 2012.
Ansel et al., Pharmaceutical Dosage Forms and Drug Delivery Systems, Lippincott Williams and Wilkins, 1999, $7^{th}$ Edition: pp. 213, 217 and 218.
Avdeef, A., et al., Journal of the American Chemical Society, 1978, 100: 5362-5370.
Baes, C.F. and Mesmer, R.E., "The Hydrolysis of Cations", Wiley, NY, pp. 226-238 1976.
Bergeron, R.J. and Brittenham, G.M., Eds, "The Development of Iron Chelators for Clinical Use", CRC Press, Boca Raton, pp. 1-4, 155-167 1994.
Brunton et al., "The Pharmacological Basis of Therapeutics," McGraw-Hill, 2006, $11^{th}$ Edition, p. 4.
Byrne, R.H. and Luo, Y.-R., Geochimica et Cosmochimica Acta, 2000, 64:1873-1877.
Chang, R., "General Chemistry, The Essential Concepts", Mcgraw Hill, NY, 684-707 2008.
Chang et al., "Effect of ferric polymaltose complex as a phosphate binder in haemodialysis patients" Nephrology Dialysis Transplantation, vol. 14, No. 4, 1999, pp. 1045-1047.
Declaration of Dr. Robert O. Williams, III, Ph.D. in Support of Plaintiffs' Opening Claim Construction Brief, dated May 1, 2019, in *Vifor Fresenius Medical Care Renal Pharma Ltd. et al. v. Lupin Atlantis Holdings SA, et al.*, C.A. No. 1:18-cv-00390-LPS in the United States District Court for the District of Delaware.
Declaration of Dr. Wesley R. Harris, Ph.D. In Support of Plaintiffs' Opening Claim Construction Brief, dated May 1, 2019, in *Vifor Fresenius Medical Care Renal Pharma Ltd. et al. v. Lupin Atlantis Holdings SA, et al.*, C.A. No. 1:18-cv-00390-LPS in the United States District Court for the District of Delaware.
Declaration Under 37 C.F.R. § 1.132 of Dr. Erik Philipp, dated Dec. 3, 2015, submitted on Dec. 11, 2015, in connection with the prosecution of U.S. Appl. No. 12/743,120.
Declaration under 37 C.F.R. § 1.132 of Dr. Erik Philipp, dated Mar. 13, 2015, submitted on Mar. 19, 2015, in connection with the prosecution of U.S. Appl. No. 12/743,120.
Declaration Under 37 C.F.R. § 1.132 of Dr. Peter Geisser, dated May 28, 2013, submitted on May 31, 2013, in connection with the prosecution of U.S. Appl. No. 12/743,120.
Defendants' Opening Claim Construction Brief, dated May 1, 2019 in *Vifor Fresenius Medical Care Renal Pharma Ltd. et al. v. Lupin Atlantis Holdings SA, et al.*, C.A. No. 18-390-LPS in the United States District Court for the District of Delaware.
Defendants' Responsive Claim Construction Brief (Redacted), dated May 24, 2019, in *Vifor Fresenius Medical Care Renal Pharma Ltd. et al. v. Lupin Atlantis Holdings SA, et al.*, C.A. No. 18-390-LPS in the United States District Court for the District of Delaware.
Encyclopedia of Pharmaceutical Technology, Marcel Dekker, Inc., 1990, vol. 2, edited by J. Swarbrick and J.C. Boylan, p. 397-417.
European Pharmacopeia 5.0 (Jan. 2005), Chapter 2.9.3 "Dissolution Test for Solid Dosage Forms" pp. 228-230.
European Pharmacopeia Fifth Edition, Supplement 5.7 (Jan. 2006), Chapter 2.9.3 "Dissolution Test for Solid Dosage Forms" pp. 4805-4814.
Fouque et al., "EBPG Guideline on Nutrition," Nephrol Dial. Transplant, May 2007, vol. 22 (Suppl 2), pp. ii45-ii87. DOI: 10.1093/ndt/gfm020.
Goodman et al., The Pharmacological Basis of Therapeutics, McGraw-Hill, 2006, $11^{th}$ Edition, edited by L.L. Brunton, Ph.D., J.S. Lazo, Ph.d., and K.L. Parker, M.D., Ph.D., p. 4.
Handbook of Pharmaceutical Excipients, Pharmaceutical Press, 2003, 4th Edition, edited by R.C. Rowe, P.J. Sheskey, and S.C. Owen, pp. 161-164; 181-183; 184-185; 235-236; 294-296; 354-357; 383-385; 404-405; 529-531; 581-584; 620-621; 641-643.
Handbook of Pharmaceutical Excipients, Pharmaceutical Press, 2006, $5^{th}$ Edition, edited by R.C. Rowe, P.J. Sheskey, and S.C. Owen, pp. 725-730,744-747.
Hergesell et al., "Efficacy of a new iron based phosphate binder in dialysis patients" Nephrology Dialysis Transplantation, 2001, vol. 16, No. 6, A90.
How et al., "Effects of Lanthanum Carbonate on the Absorption and Oral Bioavailability of Ciprofloxacin," Clin J Am Soc Nephrol., Nov. 2007, vol. 2, (6), pp. 1235-1240. DOI: 10.2215/CJN.01580407.
Hutchison, "Improving phosphate-binder therapy as a way forward," Nephrol Dial Transplant, Mar. 2004, vol. 19 (Suppl 1), pp. i19-i24.
International Search Report dated Mar. 23, 2006, in Application No. WO2006000547 (PCT/EP2005/052861).
Iron—Fact Sheet for Health Professionals, National Institutes of Health, Office of Dietary Supplements, May 23, 2019. pp. 1-29.
Kottke et al., "Tablet Dosage Forms," Modern Pharmaceutics, Marcel Dekker, Inc., 2002, $4^{th}$ Edition, edited by G.S. Banker and C.T. Rhodes, pp. 287, 293-305.
List of modifications to the Irish SmPC for Foznol® taken from (https://www.medicines.ie/medicines/foznol-250mg-500mg-750mg-1000mg-chewable-tablets-32205/) accessed on May 29, 2019.
Lozano et al., "Temperature, pH and agitation rate as dissolution test discriminators of zofenopril calcium tablets," Journal of Pharmaceutical & Biomedical Analysis, 1994, vol. 12, No. 2, pp. 173-177.
Mendes et al., "Chewable Tablets" in Pharmaceutical Dosage Forms: Tablets, Marcel Dekker, Inc., 1989, $2^{nd}$ Edition, edited by H.A. Lieberman, L. Lachman, and J.B. Schwartz, pp. 367-417.
Novelli, "Higher dose formulation of FOSRENOL® approved to reduce serum phosphorus in esrd patients," Press Release Nov. 28, 2005.
Opening Declaration of Walter G. Chambliss, Ph.D., Regarding Claim Construction, dated Apr. 26, 2019, in *Vifor Fresenius Medical Care Renal Pharma Ltd. et al. v. Lupin Atlantis Holdings SA, et al.*, C.A. No. 1:18-cv-00390-LPS in the United States District Court for the District of Delaware.
Opposition Reply Filed on May 30, 2019.
Pharmaceutical Codex 46, Walter Lund ed., 12th ed., p. 46 1994.
Pharmaceutics: The Science of Dosage Form Design, Churchill Livingstone, 2002, $2^{nd}$ Edition, edited by M.E. Aulton, pp. 389, 390 & 412 (ISBN 0 443 05517 5).

(56) References Cited

OTHER PUBLICATIONS

Plaintiffs' Opening Claim Construction Brief, dated May 1, 2019, in *Vifor Fresenius Medical Care Renal Pharma Ltd. et al.* v. *Lupin Atlantis Holdings SA, et al.*, C.A. No. 1:18-cv-00390-LPS in the United States District Court for the District of Delaware.
Plaintiffs' Responsive Claim Construction Brief, dated May 24, 2019, in *Vifor Fresenius Medical Care Renal Pharma Ltd. et al.* v. *Lupin Atlantis Holdings SA, et al.*, C.A. No. 1:18-cv-00390-LPS in the United States District Court for the District of Delaware.
Remington: The Science and Practice of Pharmacy, Mack Printing Co., 19th edition, vol. 11, 1995, pp. 1627-1628.
Remington: The Science and Practice of Pharmacy, Mack Printing Co., 19th edition, vol. 11, 1995, pp. 1616-1620.
Responsive Declaration of Dr. Robert O. Williams, III, Ph.D. In Support of Plaintiffs' Responsive Claim Construction Brief, dated May 24, 2019, in *Vifor Fresenius Medical Care Renal Pharma Ltd. et al.* v. *Lupin Atlantis Holdings SA, et al.*, C.A. No. 1:18-cv-00390-LPS in the United States District Court for the District of Delaware.
Responsive Declaration of Dr. Wesley R. Harris, Ph.D. In Support of Plaintiffs' Responsive Claim Construction Brief, dated May 24, 2019, in *Vifor Fresenius Medical Care Renal Pharma Ltd. et al.* v. *Lupin Atlantis Holdings SA, et al.*, C.A. No. 1:18-cv-00390-LPS in the United States District Court for the District of Delaware.
Ritz et al., "Compounds in development to combat hyperphosphataemia" Expert Opin. Investig. Drugs, vol. 10, No. 12, 2001, pp. 2185-2190.
Santos, M.A. et al., Journal of the Chemical Society, Dalton Transactions, 1993, 927-932.
Savica et al., "Phosphate binders and management of hyperphosphataeia in end-stage renal disease," Nephrol Dial Transplant. Aug. 2006;21 (8), pp. 2065-2068. Epub Jun. 9, 2006.
Schwertmann, U., Plant and Soil, 1991, 130: 1-25.
Schwertmann, "Iron Oxides in the Laboratory" VCH Verlagsgesellschaft GmbH, 2000, 2nd Edition,.pp. 511; 55-65.
Shangraw, "Chewable Tablets," Modern Pharmaceutics Revised and Expanded, Marcel Dekker, Inc., 1990, $2^{nd}$ Edition, edited by G.S. Banker and C.T. Rhodes, p. 438.
Sherman, "Decreased Pill Burden in Phosphate Binder Therapy," Medscape Nephrology, 2005, vol. 2(1).
Shriver, D.F. and Atkins, P.W., "Inorganic Chemistry", Freeman, NY, pp. xii-xvii 1999.
Szymanska et al., "Comparison of Flow-Through Cell and Paddle Methods for Testing Vaginal Tablets Containing a Poorly Water-Soluble Drug," Tropical Journal of Pharmaceutical Research, Feb. 2013, vol. 12(1), pp. 39-44.
Tips to Control Fluid Intake, Registered Dietitians, Dept of Veterans Affairs, 2005, pp. 1-4.
Turkoglu et al., "Tablet Dosage Forms," Modern Pharmaceutics, Informa Healthcare, 2009. $5^{th}$ Edition, edited by A.T. Florence and J. Siepmann, p. 483.
Updated Irish Summary of Product Characteristics (Sm PC) for Foznol® (Lanthanum carbonate) chewable tablets, revised Oct. 2018, pp. 1-9.
Yaguchi, "PA21, a novel phosphate binder, improves renal osteodystrophy in rats with chronic renal failure," PLoS ONE, vol. 12(7), Jul. 13, 2017, pp. 1-18.
Poster presented at ASN Kidney Week 2018, Oct. 23-28, San Diego, CA, USA.
Certified advanced training for doctors: "Hyperphosphatemia in chronic kidney disease" 2015 from https://www.my-cme.de/wp-content/uploads/arzt_hyperphosphataemie _2015.pdf.
Floege J. J Nephrol. Jun. 2016;29(3):329-340.
Black T, Philips G, Burbridge R (2013) Pharmacobezoarin a patient on an oral phosphate binder. Gastrointest Endosc 77:511-512.
Dtsch Med Wochenschr 2009; 134, Nr. 34/35.
Chuang CL, Chiou SY, Li SY, Jian DY, Chen JY. A peritoneal dialysis patient with an unusual abdominal film. Treatment with lanthanum carbonate. Kidney Int 2007; 72: 1291-1292.
Moazzam A. et al. J Kidney Dis. 2013;62(4):844-846.
Letter of the FDA to Shire dated Sep. 2, 2011.

Prescribing Information Fosrenol (lanthanum carbonate) Chewable Tablets (revised Aug. 2011).
Fischer D. et al. Am J Kidney Dis. Sep. 2006;3:437-444.
Lanz M. et al. Drug Dev Ind Pharm. Dec. 2014;40(12):1623-1631.
*Vifor Fresenius Medical Care Renal Pharma Ltd., et al.* v. *Lupin Atlantis holdings SA, et al.* Markman Decision filed Sep. 5, 2019.
Result of Oral Proceeding in EP Application No. 08848615.4, dated Jul. 31, 2019.
Notice of European Patent Office: Rejection of the Opposition to European Patent No. EP2222285 dated Oct. 29, 2019.
Defendant Annora Pharma Private Ltd., and Hetero Labs Limited's Joint Initial Invalidity Contentions, served Oct. 11, 2019, in *Vifor Fresenius Medical Care Renal Pharma Ltd. and Vifor Fresenius Medical Care Renal Pharma France S.A.S.* , v. *Annora Pharm Private Ltd. and Hetero Labs Limited*, Civil Case No. 18-cv-01996-LPS (D. Del.).
Lupin Atlantix Holdings SA's and Lupin Pharmaceuticals, Inc.'s Answer, affirmative defenses and counterclaims to first amended complaint for patent infringement, Oct. 9, 2019, in *Vifor Fresenius Medical Care Renal Pharma Ltd. and Vifor Fresenius Medical Care Renal Pharma France S.A.S.*, v. *Lupin Atlantis Holdings SA, Lupin Pharmaceuticals, Inc., and Teva Pharmaceuticals USA, Inc.*, No. 18-390-LPS (D. Del.).
Defendant Teva Pharmaceuticals USA Inc.'s first amended answer, affirmative defenses and counterclaims, Oct. 9, 2019, in *Vifor Fresenius Medical Care Renal Pharma Ltd. and Vifor Fresenius Medical Care Renal Pharma France S.A.S.*, v. *Lupin Atlantis Holdings SA, Lupin Pharmaceuticals, Inc., and Teva Pharmaceuticals USA, Inc.*, No. 18-390-LPS (D. Del.).
Answering brief in opposition to plaintiffs motion to dismiss defendant's inequitable conduct counterclaims under Fed. R. Civ. 12(b)(6), Dec. 6, 2019, in *Vifor Fresenius Medical Care Renal Pharma Ltd. and Vifor Fresenius Medical Care Renal Pharma France S.A.S.*, v. *Lupin Atlantis Holdings SA, Lupin Pharmaceuticals, Inc., and Teva Pharmaceuticals USA, Inc.*, No. 18-390-LPS (D. Del.).
Declaration of Richard c. Pettus in support of defendants' answering brief in opposition to Plaintiffs' motion to dismiss defendants' Inequitable conduct counterclaims under fed. R. Civ. P. 12(b)(6), Dec. 6, 2019, in *Vifor Fresenius Medical Care Renal Pharma Ltd. and Vifor Fresenius Medical Care Renal Pharma France S.A.S.*, v. *Lupin Atlantis Holdings SA, Lupin Pharmaceuticals, Inc., and Teva Pharmaceuticals USA, Inc.*, No. 18-390-LPS (D. Del.).
Deposition of Vifor by and through Erik Philipp, Sep. 12, 2019, New York, in *Vifor Fresenius Medical Care Renal Pharma Ltd. and Vifor Fresenius Medical Care Renal Pharma France S.A.S.*, v. *Lupin Atlantis Holdings SA, Lupin Pharmaceuticals, Inc., and Teva Pharmaceuticals USA, Inc.*, No. 18-390-LPS.
Reply expert report of Walter G. Chambliss, PhD, Dec. 23, 2019 , in *Vifor Fresenius Medical Care Renal Pharma Ltd. and Vifor Fresenius Medical Care Renal Pharma France S.A.S.*, v. *Lupin Atlantis Holdings SA, Lupin Pharmaceuticals, Inc., and Teva Pharmaceuticals USA, Inc.*, No. 18-390-LPS (D. Del.).
Opening expert report of Walter G. CHambliss, PhD, Nov. 1, 2019, in *Vifor Fresenius Medical Care Renal Pharma Ltd. and Vifor Fresenius Medical Care Renal Pharma France S.A.S.*, v. *Lupin Atlantis Holdings SA, Lupin Pharmaceuticals, Inc., and Teva Pharmaceuticals USA, Inc.*, No. 18-390-LPS (D. Del.).
Plaintiffs' motion to dismiss defendants' inequitable conduct counterclaims under Fed. R. Civ. 12(b)(6), Nov. 13, 2019, in *Vifor Fresenius Medical Care Renal Pharma Ltd. and Vifor Fresenius Medical Care Renal Pharma France S.A.S.*, v. *Lupin Atlantis Holdings SA, Lupin Pharmaceuticals, Inc., and Teva Pharmaceuticals USA, Inc.*, No. 18-390-LPS (D. Del.).
Rebuttal expert report of Dr. Ajay Rastogi, MD, PhD, Dec. 4, 2019, in *Vifor Fresenius Medical Care Renal Pharma Ltd. and Vifor Fresenius Medical Care Renal Pharma France S.A.S.*, v. *Lupin Atlantis Holdings SA, Lupin Pharmaceuticals, Inc., and Teva Pharmaceuticals USA, Inc.*, No. 18-390-LPS (D. Del.).
Rebuttal expert report of Professor Robert O. Williams III, PhD, Dec. 4, 2019, in *Vifor Fresenius Medical Care Renal Pharma Ltd. and Vifor Fresenius Medical Care Renal Pharma France S.A.S.*, v.

(56) References Cited

OTHER PUBLICATIONS

*Lupin Atlantis Holdings SA, Lupin Pharmaceuticals, Inc., and Teva Pharmaceuticals USA, Inc.*, No. 18-390-LPS (D. Del.).
Rebuttal expert report of Dr. Weslet R. Harris, PhD regarding validity,Dec. 4, 2019, in *Vifor Fresenius Medical Care Renal Pharma Ltd. and Vifor Fresenius Medical Care Renal Pharma France S.A.S., v. Lupin Atlantis Holdings SA, Lupin Pharmaceuticals, Inc., and Teva Pharmaceuticals USA, Inc.*, No. 18-390-LPS (D. Del.).
Expert report of Carla S. Mulhern, Dec. 4, 2019, in *Vifor Fresenius Medical Care Renal Pharma Ltd. and Vifor Fresenius Medical Care Renal Pharma France S.A.S., v. Lupin Atlantis Holdings SA, Lupin Pharmaceuticals, Inc., and Teva Pharmaceuticals USA, Inc.*, No. 18-390-LPS (D. Del.).
Reply expert report of Robert Linhardt, PhD, Dec. 20, 2019, in *Vifor Fresenius Medical Care Renal Pharma Ltd. and Vifor Fresenius Medical Care Renal Pharma France S.A.S., v. Lupin Atlantis Holdings SA, Lupin Pharmaceuticals, Inc., and Teva Pharmaceuticals USA, Inc.*, No. 18-390-LPS (D. Del.).
Reply expert report of Stephen Z. Fadem, MD, Dec. 22, 2019, in *Vifor Fresenius Medical Care Renal Pharma Ltd. and Vifor Fresenius Medical Care Renal Pharma France S.A.S., v. Lupin Atlantis Holdings SA, Lupin Pharmaceuticals, Inc., and Teva Pharmaceuticals USA, Inc.*, No. 18-390-LPS (D. Del.).
Plaintiffs' reply in support of their motion to dismiss defendants' inequitable conduct counterclaims under Fed. R. Civ. P. 12(b)(6), Dec. 23, 2019, in *Vifor Fresenius Medical Care Renal Pharma Ltd. and Vifor Fresenius Medical Care Renal Pharma France S.A.S., v. Lupin Atlantis Holdings SA, Lupin Pharmaceuticals, Inc., and Teva Pharmaceuticals USA, Inc.*, No. 18-390-LPS (D. Del.).
Expert report of DeForest McDuff, PhD, Dec. 23, 2019, in *Vifor Fresenius Medical Care Renal Pharma Ltd. and Vifor Fresenius Medical Care Renal Pharma France S.A.S., v. Lupin Atlantis Holdings SA, Lupin Pharmaceuticals, Inc., and Teva Pharmaceuticals USA, Inc.*, No. 18-390-LPS (D. Del.).
U.S. National Phase Filing of PCT/EP/96/05695.
Brennan et al., The cost-effectiveness of lanthanum carbonate in the treatment of hyperphosphatemia in patients with end-stage renal disease, Value in Health, vol. 10, No. 1, 2007, pp. 32-41.
Bolhuis et al., Excipients for direct compaction—an update, Pharmaceutical Development and Technology, vol. 11, 2006, pp. 111-124.
Brunton et al., "The Pharmacological Basis of Therapeutics," McGraw-Hill, 2006, 11th Edition, p. 4. pp. 1-39.
Dollery, Therapeutic Drugs, Churchill Livingstone, 1991, Edinburgh.
Filho et al., Calcium acetate versus calcium carbonate in the control of hyperphosphatemia in hemodialysis patients, Sao Paulo Medical Journal, 2000, vol. 118, No. 6, 2000, pp. 179-184.
Giesser et al., Structure/Histotoxicity relationship of parenteral iron preparations, Arneim-Forsch.Drug Res., vol. 42 (II), No. 12, 1992, pp. 1439-1452.
Guidance for Industry Dissolution testing of immediate release solid oral dosage forms, FDA Center for drug evaluation and research, 1997.
Lieberman and Lachman, "Pharmaceutical Dosage Forms: Tablets", vol. 1, pp. 68-99, 109-185, 1980, Marcel Dekker Inc, New York.
Manudhane et al., Tableting properties of a directly compressible starch, Journal of Pharmaceutical Sciences, vol. 58, No. 5, 1969, pp. 616-620.
Pennick et al., Absolute bioavailability and disposition of lanthanum in healthy human subjects administered lanthanum carbonate, J Clin Pharmacol, 2006, vol. 46, pp. 738-746.
Phosphate adsorber project, Progress report and minutes of meeting of Nov. 18, 1993.
Phosphate adsorber project, Meeting log of Apr. 27, 1994.
Pray W.S., Nonprescription Product Therapeutics, Lippin cott William & Wilkins, 1999, Philadelphia, pp. 82-88.
Project PA21: Business analysis and planning Jun. 2004.
Remington's Pharmaceutical Sciences, 15th ed., Mack Publishing Company, edited by Arthur Osol, (1975), pp. 1571-1575.
Ritz et al. Oral phosphate binders without aluminium and calcium—a pipe dream? Nephrol Dial Transplant, 1996, vol. 11, pp. 766-768.
Schwartz et al., Intragranular Starch: Comparison of Starch USP and Modified Cornstarch, Journal of Pharmaceutical Sciences, vol. 35, No. 2, 1975, pp. 328-332.
Spengler et al., Cross-linked iron dextran is an efficient oral phosphate binder in the rat, Nephrology Dialysis Transplantation, 1996, vol. 11, pp. 808-812.
Defendants' Joint Initial Invalidity Contentions, served Jan. 14, 2019, in *Vifor Fresenius Medical Care Renal Pharma Ltd. and Vifor Fresenius Medical Care Renal Pharma France S.A.S., v. Lupin Atlantis Holdings SA, Lupin Pharmaceuticals, Inc., and Teva Pharmaceuticals USA, Inc.*, No. 18-390-LPS (D. Del.).
Remington's Pharmaceutical Sciences, 16th ed., Mack Publishing Company, edited by Arthur Osol, (1980), pp. 1553-1565 and 1585.
Handbook of Pharmaceutical Excipients, 3rd ed., edited by A. H. Kibbe, American Pharmaceutical Association, 2000.
Olaf Hergesell & Eberhard Ritz, Phosphate binders on iron basis: A new perspective?, Kidney International, vol. 56, Suppl. 73 (1999), pp. S-42-S-45.
Ralph F. Shangraw, Compressed Tablets by Direct Compression, in 1 Pharmaceutical Dosage Forms: Tablets, vol. 1, 195 (Herbert A. Lieberman et al., 2d ed. 1989), pp. 195-246.
Howard C. Ansel, Nicholas G. Popovich, and Loyd V. Allen, Jr., *Pharmaceutical Dosage Forms and Drug Delivery Systems* (6th ed. 1995), 99. 212-13.
James Swarbrick & James C. Boylan, *Encyclopedia of Pharmaceutical Technology*, 397-415 (vol. 2, 1990).
Chemistry: The Central Science, Theodore L. Brown et al, 7th Edition, (1997), cover page.
Appeal to the Decision Rejecting the Opposition to European Patent No. EP2222285, dated Apr. 16, 2020.
Declaration of Dr. Francisco Marquillas Olondriz for submission in appeal proceedings against European Patent No. EP2222285, dated Apr. 16, 2020.

* cited by examiner

PHARMACEUTICAL COMPOSITIONS

FIELD OF THE INVENTION

This invention relates to pharmaceutical compositions comprising iron oxy-hydroxide in high loading in a form suitable for oral administration, and in particular for administration as an oral delivery system either as dosage forms for intact swallowing (e.g. film-coated) or as dosage forms capable of rapid disintegration, as well as methods of production thereof.

BACKGROUND

In patients with chronic renal insufficiency, a pathologically increased serum phosphate level occurs due to the decrease in the glomerular filtration rate. The secondary hyperparathyroidism which sets in therewith must be considered as one of the causes of the occurrence of renal osteopathy. Attempts are normally made to maintain the phosphate balance in equilibrium by dialysis or by the administration of oral phosphate adsorbers which suppress the resorption of foodstuff phosphates in the gastrointestinal tract, or by the combination of both methods, but with the current state of the art this is either not efficient enough, is not economic, or is burdened with side effects.

Recently new and effective phosphate adsorbers based on iron oxy-hydroxide, in particular containing beta-iron oxy-hydroxide stabilised by a stabilization agent such as a carbohydrate and/or humic acid, have been described (EP 0 868 125). These adsorbers show superior phosphate adsorption capacity from aqueous solutions, for example for the adsorption of inorganic phosphates and phosphates bonded to foodstuffs (EP 0 868 125) and have been shown to be efficient oral phosphate binders in the treatment of hyperphosphataemia (Neophrol. Dial. Transplant 14, 863, 1999).

To achieve maximum efficiency while maintaining good patient compliance, it is desirable that such adsorbers can be administered in high dosages. However, phosphate adsorbers with high iron loadings are still not available. Factors, such as ease of administration in general, unacceptable taste, as well as storage and stability problems, limit the applicability of currently available phosphate binders.

WO 2006/000547 of the present applicant discloses a process for preparing an iron-sulfate based phosphate adsorbent, which may be used for preventing and treating hyperphosphatemic conditions. Described are iron oxy hydroxide compositions which are prepared form ferric sulphate and/or nitrate containing a stabilising agent selected from humic acid and carbohydrates and which have an iron content of at most 20.3 to 22.3% by weight. These compositions are obtained by rotary evaporation. No specific oral formulations such as tablets are disclosed. It is explained that the iron compositions can be formulated to tablets or other oral formulations together with usual excipients and adjuvants. This means that tablets obtained from the iron oxy hydroxide compositions can have an iron content of at most 20% (w/w) corresponding to 32% (w/w) iron oxy-hydroxide.

EP 1 757 299 of the present applicant describes iron(III) carbohydrate complex compounds and there use for orally or parenterally treating iron deficiency in patients having chronic inflammatory bowel disease. In the document reference is made to Maltofer® film tablets containing 100 mg iron(III). The iron content of the tablet is 16% by weight corresponding to 25.6% w/w iron oxy-hydroxide. The preparation is intended for treating iron deficiency, that is, for liberating iron(III), contrary to phosphate adsorbents as defined in the present invention. No drying procedure is described.

WO 92/01458 discloses oxy-iron compounds, in particular iron oxides, iron hydroxides and iron oxy hydroxides which are formulated as a therapeutic dosage form for use as a phosphate adsorber. No specific oral formulations are disclosed, and no specific iron loading is mentioned. Further, no excipients and manufacturing methods are specifically disclosed, but reference is made to "acceptable methods and excipients". It is said that each oral dose may contain 50 mg to about 500 mg or more of oxy-iron compound. According to the state of the art tablets containing 500 mg oxy-iron compounds, which are necessary in order to achieve a desired degree of phosphate adsorption, would be of such an enormous size that they could not be swallowed by the patient. The document does not disclose anything as to obtaining a high iron loading.

U.S. Pat. No. 5,514,281 discloses polynuclear iron oxy hydroxides bound to a support such as saponified divinylethylene urea vinylacetate copolymer, Lewatit R®, silica, glasses and organic porous supports modified with dextran. The maximum iron loading of a support carrying iron(III) is reported to be 29.3% by dry weight. The product is formed from a dry support, which is swelled, and it may not be dried thereafter since otherwise removal of phosphate from the dialysate would not work at all.

None of the examples in U.S. Pat. No. 5,514,281 describes a dry/tablet formulation for oral administration. The examples given describing adsorbents are all meant for extracorporal use and none of the supports used for their production is applicable for medicinal use. The preparation of an oral formulation is only described as "pressed into powder for . . . ". These products are developed to release iron.

For a wide range of drugs, oral dosage forms such as tablets are clearly the preferred form of delivery. This is due to a high level of patient acceptability and compliance (because they provide an accurate dosage and are easy to administer) as well as advantageous characteristics during and after manufacture, such as they typically show satisfactory physical and chemical stability, are convenient for packing, shipping and administering and offer advantages in manufacturing speed and cost.

However, oral dosage forms need carefully designed disintegration characteristics to achieve the desired bioavailability for the incorporated drug, i.e. dissolution must precede absorption, in case of immediate release tablets should disintegrate rapidly after ingestion in order to facilitate dissolution of the drug. Moreover, the drug loading of conventional tablet formulations is often limited due to potential gastrointestinal irritation (caused by locally high concentration) and/or patient compliance (which limits size and shape to achieve easy swallowing).

These limitations have prevented the development of an effective oral delivery system for iron oxy-hydroxide as phosphate binder with high loadings.

Applicants have now found that iron oxy-hydroxide (hereinafter also referred to as active agent), and in particular iron oxy-hydroxide containing beta-iron oxy-hydroxide, and in particular further containing a carbohydrate and/or humic acid that may act as a stabilization agent as described in EP 0 868 125 B1, can be successfully formulated in form of an oral delivery system with high loadings (hereinafter also called pharmaceutical compositions or compositions of the invention), preferably either as dosage forms for intact swallowing (e. g. film-coated) or as dosage forms capable of rapid disintegration (either in the oral cavity or in a small amount of liquid prior to ingestion). Thus the pharmaceutical compositions of the invention are able to achieve both high loadings and suitable disintegration characteristics while maintaining a minimal size and thus are able to overcome the drawbacks of currently known formulations.

The inventive compositions have a low iron release rate of below 2.5% w/w, which is essential for phosphate adsorbers. In contrast thereto, compositions used for treating iron deficiency have a high iron release rate and thus are completely different form the inventive compositions.

Furthermore it was found that the pharmaceutical compositions of the invention can be preferably obtained through conventional molding or tabletting methods, more preferably direct compression tabletting methods, in the presence of one or more excipients fulfilling for example the functions of binder and/or filler and/or disintegrant in one.

It was further found that any disagreeable taste associated with the active agent, if administered as dosage forms capable of disintegration in the oral cavity, can be eliminated using suitable taste-masking agents, sweeteners and/or taste-enhancing agents.

Further it was found that favourable tablet formulations with a particularly high iron-oxy-hydroxide-load can be obtained, if they are comprised of substantial amounts of a flowable powder that has been prepared by spray-drying an aqueous suspension of the ingredients.

SUMMARY OF THE INVENTION

It is an object of the invention to provide pharmaceutical compositions comprising iron oxy-hydroxide in a form suitable for oral administration, in particular as an oral delivery system with high loadings, preferably either as dosage forms for intact swallowing (e.g. film-coated) or as dosage forms capable of rapid disintegration (either in the oral cavity or in a small amount of liquid prior to ingestion).

In a preferred embodiment the iron oxy-hydroxide-containing pharmaceutical composition comprises one or more carbohydrates and/or humic acid, preferably a carbohydrate such as a mono- di- or polysaccharide, preferably saccharose (sucrose), starch, agarose, dextran, dextrin, cellulose and derivatives of each of these. Those carbohydrates and/or humic acid may act as a stabilization agent as described in EP 0 868 125 B1. Apart from this or in addition to this the carbohydrate(s) and/or humic acid may act as a binder and/or filler and/or disintegrant.

In yet another embodiment the compositions of the invention comprise one or more taste-masking and/or coloring additives such as flavouring agents, sweeteners, taste-enhancing agents, colorants, and the like.

Depending on the intended use of the tablet, i.e. whether it is for intact swallowing or rapid disintegration (in the oral cavity or in a small amount of liquid prior to ingestion), such as e.g. a chewable tablet, usual excipients, such as superdisintegrants, glidants, lubricants, antioxidants compression aids and the like may be added if desired. The tablet may be coated with usual film-forming agents, if desired.

In another embodiment, the pharmaceutical compositions of the invention are in any dosage form suitable for oral administration and in particular include tablets and pills, either in a form for intact swallowing (e.g. film-coated) or in a form capable of rapid disintegration (either in the oral cavity after ingestion or in a small amount of liquid prior to ingestion), including a chewable form, dry powders, granules, capsules or sachets containing these, granules, wafers, films, lozenges, and the like.

It is a further object of the invention to provide methods for formulating an oral delivery system according to the invention, in particular an oral delivery system either as dosage forms for intact swallowing (e.g. film-coated) or as dosage forms capable of rapid disintegration (either in the oral cavity or in a small amount of liquid prior to ingestion), comprising iron oxy-hydroxide in high loadings, by means of conventional molding or tabletting methods, preferably direct compression tabletting methods.

DETAILED DESCRIPTION OF THE INVENTION

Thus, in a first aspect the present invention is directed to pharmaceutical compositions comprising iron oxy-hydroxide as an active agent in high loadings and in a form suitable for oral administration showing the desired disintegration characteristics.

In particular, the present invention is directed to such orally administrable, pharmaceutical compositions with high loadings of the active agent, either as dosage forms for intact swallowing (e.g. film-coated) or as dosage forms capable of rapid disintegration (either in the oral cavity or in a small amount of liquid prior to ingestion).

As indicated hereinabove, the term "active agent" as used herein includes iron(III)-oxy-hydroxide. Iron(III)-oxy-hydroxide or iron(III)-oxide-hydroxide is usually referred to as $FeO(OH)$ or $Fe_2O_3 \times H_2O$. Such iron oxy-hydroxides to be used in accordance with the present invention are usually formed upon hydrolysis and precipitation in aqueous iron (III)-salt solutions (see, for example, Römpp Lexikon Chemie, 10. Auflage, 1997; U. Schwertmann, R. M. Cornell "Iron Oxides in the Laboratory", VCH Verlagsgesellschaft mbH, 1991, Seiten 95-100). The term "iron oxy-hydroxide" as used herein thus includes, in particular, alpha, beta, gamma, and delta FeOOH and mixtures thereof. Preferably, the iron oxy-hydroxide comprises beta FeOOH optionally in admixture with other iron oxy-hydroxide(s).

Iron oxy-hydroxides to be used in accordance with the present invention are preferably prepared by adding a base to an aqueous iron(III)-salt solution as described in EP 0868125 B1, and subsequent drying.

Preferably iron oxy-hydroxide stabilized by a stabilization agent is used.

The wording "iron oxy-hydroxide, which is stabilized by a stabilization agent" includes preferably an iron oxy-hydroxide together with a stabilization agent, which includes in particular carbohydrates and humic acid. As described in EP 0868125 B1 such stabilization agent usually is not bound as a complex compound to the iron oxy-hydroxide, which means for example that a water-soluble stabilization agent can be removed by washing the stabilized iron oxy-hydroxide with water. As further described in EP 0868125 B1 the stabilization agent is supposed to stabilize the iron oxy-hydroxide against ageing, thereby preserving its phosphate adsorption capacity. This means that a stabilized iron oxy-hydroxide in general has a higher phosphate adsorption capacity (as measured in EP 0868125 B1) compared to a non-stabilized iron oxy-hydroxide. In a accordance with the present invention a preferred "iron oxy-hydroxide, which is stabilized by a stabilization agent" comprises beta iron oxy-hydroxide stabilized as described in EP 0868125 B1 with at least one carbohydrate and/or humic acid.

Generally, due to their chemical nature the iron oxy-hydroxides used and administered in accordance with the present invention essentially are not absorbed by the human body, i.e. they are essentially non-bioabsorbable.

Accordingly the term "stabilization agent" as used herein includes preferably at least one carbohydrate and/or humic acid, in particular, as described in EP 0868125 B1. In one embodiment, the at least one carbohydrate is soluble and includes at least one mono-, di- or polysaccharide, such as agarose, dextran, dextrin, dextran derivatives, cellulose and cellulose derivatives, saccharose (sucrose), maltose or lactose preferably saccharose (sucrose), dextrin or starch.

The term "starch" as used herein includes any conventionally used starch products (such as potato starch, corn starch, rice starch, tapioca starch) in native, pregelatinized, degraded, modified, and derivatized forms, preferably suitable for direct compression, and mixtures thereof.

Preferred products include native and pregelatinized starch, such as in a mixture having a ratio (native:pregelatinized) in the range of 10:1 to 0.5:1, preferably in the range of 3:1 to 0.5:1 more preferably in the range of 2:1 to 1:1. The use of a mixture of native and pregelatinized starch has turned out be particularly advantageous in the manufacture of a tablet with high iron loading, since it allows the preparation of a stabilized pre-mixture which can be compressed to a suitable tablet either directly or with a very small amount of further excipients.

In one specific embodiment the stabilization agent of choice may be present in an amount of 1.0 to 50% (w/w), preferably 5.0 to 30% (w/w).

All % weights (w/w) throughout this description are expressed in relation to the total weight of the pharmaceutical composition, if not indicated otherwise.

The term "high loading" as used herein indicates that the iron oxy-hydroxide is present in an amount of 10 to 80% (w/w), more preferably 30 to 65% (w/w).

The content of iron oxy-hydroxide is calculated as approximately 1.6× content of iron.

Thus, the values mentioned above correspond to a content of iron of 6 to 50% w/w, more preferably 19 to 41% (w/w).

In preferred embodiments of the invention even higher iron loadings are realized, namely more than 50% (w/w) to 90% (w/w) iron oxy-hydroxide, preferably 56%-65% (w/w) corresponding to 31 to 56% (w/w), preferably 35% to 41% (w/w) iron.

Or else, the iron oxy-hydroxide is preferably present in an amount of >300 mg per dosage form, more preferably 300 to 2000 mg per dosage form. It is understood that the amount of active agent depends on the intended administration route, i.e. the amount present in tablets for intact swallowing film coated e.g. film-coated) are preferably 350 to 850 mg whereas the amount present in oral dosage forms capable of rapid disintegration (either in the oral cavity or in a small amount of liquid prior to ingestion) are preferably 700 to 1700 mg.

In addition to the active agent, conventional pharmaceutical compositions typically contain a number of additional inactive ingredients known as excipients and/or additives. In particular when the amount of active agent required to accomplish a desired therapeutic, nutritive or chemical effect is very small, the presence of inert diluents, fillers, binders, excipients and disintegrants, lubricants, glidants, and sweeteners, taste masking agents, colorants, and the like usually is critical to ensure the practicality and convenience of making oral dosage forms to achieve accurate and effective administration of the active agent.

In contrast, in case of orally administered pharmaceutical compositions having high loadings of active agent, as in the present invention, such additional inactive ingredients are minimized, since the size of an orally administered pharmaceutical composition is a critical feature for achieving good patient compliance.

As explained above, a carbohydrate such as a mono- di- or polysaccharide, preferably saccharose (sucrose), starch, agarose, dextran, dextrin, cellulose and derivativesof each of these, more preferably saccharose (sucrose), dextrin or starch may, apart from or in addition to its stabilizing effect on the iron-oxy hydroxide, act as a binder and/or filler and/or disintegrant in the pharmaceutical composition of the present invention.

Thus, a preferred composition of the invention may comprise iron oxy-hydroxide inthe amounts specified above, a stabilization agent of choice in an amount of 1.0 to 50% (w/w), preferably 5.0 to 30% (w/w), and an excipient of choice, different from the stabilizing agent, in an amount of 1.0 to 50% (w/w), preferably 5.0 to 30% (w/w), each expressed in relation to the total weight of the composition.

In another embodiment the compositions of the invention comprise one or more taste-masking and coloring additives such as flavouring agents, sweeteners, taste-enhancing agents, colorants, and the like, which are typically used for oral dosage forms.

Taste-masking agents, such as a taste-enhancing agent, flavouring agent, and/or natural or unnatural sweetener, including intense sweetener, are incorporated into oral dosage forms, such as chewable dosage forms, to give them a more pleasant taste or to mask an unpleasant one.

Typical sweeteners include, but are not limited to, a sugar which is dextrose, sucrose, fructose, lactose, confectionery sugar, powdered sugar, or is a polyol which is sorbitol (e.g. Neosorb), xylitol, maltitol, maltose and polydextrose, or a mixture thereof. Typical intense sweeteners may include, but not be limited to, aspartame, sucralose, acesulfamine K, and/or saccharin derivatives, or a mixture thereof. Further suitable sweeteners or taste-enhancing agents include glycosides such as neohesperidin dihydrochalcone (neohesperidin DC or NHDC), glycyrrhizin, glutamate, and the like. The latter may be used in very small quantities and thus may hereinafter also be called taste-enhancing agents. All the above are suitable to be used alone or as mixtures with other sweeteners and/or flavouring agents. These substances insure great lingering of the sweet taste and cover any undesired aftertaste. Preferred sweeteners and/or taste-enhancing agents include glycosides such as neohesperidin dihydrochalcone.

In one embodiment the sweetener of choice may be present in an amount of 0.01 to 2.5% (w/w), preferably 0.1 to 1.5% (w/w), most preferably 0.2 to 1.0% (w/w), in relation to the total weight of the composition.

The taste-enhancing agent of choice may be present in an amount of 0.1 to 50 ppm, preferably 1 to 10 ppm, most preferably 1 to 5 ppm, in relation to the total weight of the composition.

Typical flavouring agents include any natural and unnatural flavouring agent suitable for pharmaceutical applications, such as flavouring agents derived from a spice, fruit or fruit juice, vegetable or vegetable juice, and the like, for example flavours based on cocoa, caramel, vanilla, apple, apricot, berry (e.g. blackberry, red currant, black currant, strawberry, raspberry, woodberry, etc.), mint, panettone, honey, nut, malt, cola, verveine (verbena) or any combination thereof, such as for example caramel/vanilla, fruit/cream (e.g. strawberry/cream)and the like.

In one embodiment the flavouring agent of choice may be present in an amount of 0.01 to 10% (w/w), preferably 0.1 to 5% (w/w), most preferably 0.1 to 1% (w/w), in relation to the total weight of the composition.

Thus, another composition of the invention may comprise iron oxy-hydroxide in the amounts specified above, a stabilization agent of choice in an amount of 1.0 to 50% (w/w), preferably 5.0 to 30% (w/w), an excipient of choice, different from the stabilization agent, in an amount of 1.0 to 50% (w/w), preferably 5.0 to 30% (w/w), and taste-enhancing agent of choice, which may be present in an amount of 0.1 to 50 ppm, preferably 1 to 10 ppm, most preferably 1 to 5 ppm, and/or a flavouring agent of choice, which may be present in an amount of 0.01 to 10% (w/w), preferably 0.1 to 5% (w/w), most preferably 0.1 to 1% (w/w), each in relation to the total weight of the composition.

In yet another embodiment excipients, such as superdisintegrants, glidants, lubricants, antioxidants and the like may be added to the compositions of the invention if desired, depending on the intended use of the tablet, i.e. whether it is for intact swallowing or rapid disintegration (in the oral cavity or in a small amount of liquid prior to ingestion).

Thus in a particular embodiment the compositions of the invention may further comprise a superdisintegrant.

The term "superdisintegrant" as used herein refers to a group of disintegration agents well-known to a person skilled in the art, which can be used in a fractional amount of normal disintegrants to obtain the same effect of facilitating the disintegration or "breakup" of the dosage form after administration. Suitable examples include but are not limited to cross-linked polyvinylpyrrolidones (commercially available as Kollidon® CL and Polyplasdone® XL), particularly crospovidone®, modified starches, particularly sodium starch glycolate (commercially available under the trade names Primojel® and Explotab®), Starch 1500, modified celluloses, particularly croscarmellose sodium (cross-linked sodium carboxymethylcellulose, commercially available under the trade name Ac-Di-Sol), LHPC (Low substituted hydroxypropylcellulose) and Veegum®. Preferred examples for use in the tablet according to the invention include cross-linked polyvinylpyrrolidones and modified starches, particularly sodium starch glycolate.

According to the invention, the superdisintegrant will be present in the tablet in an amount of 0.1 to 10% (w/w), preferably 0.5 to 8% (w/w), more preferably 2.5 to 6% (w/w), in relation to the total weight of the composition. The superdisintegrant may be a single superdisintegrant or a combination of superdisintegrants or may be used in combination with one or more common disintegrants, such as for example starches, methylcellulose, calcium carboxymethylcellulose, sodium carboxymethylcellulose, hydroxypropyl cellulose, microcrystalline cellulose, colloidal silicon dioxide, croscarmellose sodium, pregelatinized starch, clays, cellulose, powdered cellulose, pregelatinized starch, sodium alginate, alginic acid, guar gum, magnesium aluminum silicate, polacrilin potassium, and the like.

Thus, another composition of the invention may comprise iron oxy-hydroxide in the amounts specified above, a stabilization agent of choice in an amount of 1.0 to 50% (w/w), preferably 5.0 to 30% (w/w), an excipient of choice, different from the stabilization agent, in an amount of 1.0 to 50% (w/w), preferably 5.0 to 30% (w/w), said excipient comprising a superdisintegrant in an amount of 0.1 to 10%, preferably 0.5 to 8% (w/w), more preferably 2.5 to 6% (w/w), and a taste-enhancing agent of choice in an amount of 0.1 to 50 ppm (w/w), preferably 1 to 10 ppm (w/w), more preferably 1 to 5 ppm (w/w), and/or a flavouring agent of choice in an amount of 0.01 to 10% (w/w), preferably 0.1 to 5% (w/w), more preferably 0.1 to 1% (w/w), all weight ranges are in relation to the total weight of the composition.

In yet another embodiment the compositions of the invention may further comprise a glidant and/or lubricant.

The term "glidant" and/or "lubricant" as used herein refers to a group of additives that are used to facilitate tablet manufacture by achieving suitable flowability, compressability, and the like. Examples of suitable glidants include, but are not limited to, magnesium oxide, magnesium stearate, calcium stearate, stearic acid, glyceryl behenate, glyceryl monostearate, glyceryl palmitostearate, hydrogenated castor oil, hydrogenated vegetable oil type I, sodium benzoate, sodium lauryl sulfate, sodium stearyl fumarate, polyethylene glycol, talcum, zinc stearate, silica derivatives, such as colloidal silica (e.g. Aerosil®) pyrogenic silica, hydrated sodium silicoaluminate, colloidal silicon dioxide, and mineral oil and light mineral oil.

Preferred glidants include magnesium oxide, magnesium stearate, talcum, colloidal silica.

In one embodiment the glidant of choice may be present in an amount of 0.01 to 10% (w/w), preferably 0.1 to 5% (w/w), most preferably 1 to 2% (w/w), in relation to the total weight of the composition.

Further additives specifically used for oral dosage forms capable of rapid disintegration in the oral cavity, may include salivating agents (compounds that are able to stimulate production of saliva) to ease swallowing. These are in general pharmaceutically acceptable acids, for example citric acid, malic acid, tartrate, or the compounds Optamint® and Optaflow®. Care has to be taken that iron release is not increased by the use of such acidic compounds, e.g. citric acid, and the amount of these substances therefore has to chosen suitably. In one embodiment the acid of choice may be present in an amount of 0.01 to 10% (w/w), preferably 0.1 to 5% (w/w), most preferably 2 to 5% (w/w), in relation to the total weight of the composition.

As mentioned hereinabove, the pharmaceutical compositions are in a form suitable for oral administration for the selective removal of inorganic phosphate, and in particular for administration as an oral delivery system either as film-coated dosage forms for intact swallowing or as dosage forms capable of disintegration (in the oral cavity or in a small amount of liquid prior to ingestion).

Thus, the pharmaceutical composition of the invention include any dosage form suitable for oral administration and in particular may include tablets and pills, either in a form for intact swallowing (e.g. film-coated) or in a form capable of rapid disintegration (either in the oral cavity after ingestion or in a small amount of liquid prior to ingestion), including a chewable form, dry powders, granules, capsules or sachets containing these granules, wafers, lozenges, and the like. The form for intact swallowing may be film-coated, if desired.

Preferred dosage forms include tablets and pills, either in a form for intact swallowing (e.g. film-coated) in or in a chewable form, granules and capsules or sachets containing these granules, and lozenges.

In the case of orally administrable dosage forms, if desired film-coated, these are swallowed intact and disintegration takes place in the stomach, whereupon the active agent is released for adsorption of phosphate to reduce its systemic uptake.

The term "film-coated" as used herein relates to a mixture of pharmaceutically acceptable excipients which is typically applied to a compressed tablet, beads, granules, or particles of active ingredient that are compressed into tablets. Alternatively it may also be combined with, mixed with or otherwise added to the active agent. It is understood that the coating chosen must be compatible with the active agent. It is further understood that a person skilled in the art will know how to manipulate the coating to achieve disintegration in the stomach by choosing the excipients which make up the coating, its type, and/or its thickness.

In a preferred embodiment the film coating is applied to a pharmaceutical composition comprising the iron oxyhydroxide and at least one excipient in compressed form.

Suitable polymers for film-coating according to the present invention are soluble at pH of from about 1.2 to about 5, such as for example hydroxypropylmethylcellulose (HPMC) alone and/or in combination with hydroxypropylcellulose (HPC), carboxymethylcellulose, methylcellulose, ethylcellulose, acrylic resins, and polyvinylpyrrolidone and gelatin or other commercially available film-coating preparations such as Dri-Klear® (Crompton & Knowles Corp., Mahwah, N.J.) or Opadry® (Colorcon, West Point Pa.).

The preferred film coating of this invention is comprised of a commercial film-coating product designed for aqueous film coating containing the water-soluble, film-forming resin, hydroxypropyl methylcellulose and polyethylene glycol (or other suitable plasticizing agents such as propylene glycol or glycerine) and optionally containing titanium dioxide (or other colorant or opacifying agent). Such a product is commercially available under the trade name Opadry® White (Colorcon, West Point, Pa.).

A suitable blend for coating may comprise 0 to about 20% w/w titanium dioxide or colorant, about 5 to about 95% w/w hydroxypropyl methylcellulose, and 0 to about 25% w/w polyethylene glycol. The most preferred embodiment comprises 10.5% non-water additives, of which 7.5% is Opadry®, in relation to the total weight of the coating.

This blend for coating may further comprise flavoring agents, taste-masking agents and salivating agents as defined hereinabove, in small amounts such as for example 0.1 to 1.0% (w/w), preferably 0.1 to 0.4% based on the weight of the total blend for coating. The preferred flavoring and/or taste-masking agent may be selected from the group of agents as defined hereinabove. The preferred amount is readily determined by balancing the goal of adding an amount sufficient to mask the core tablet taste and provide a distinct, characteristic and pleasing taste, and the goal of keeping the tablet from being too much like a candy product. The desired strength of the flavoring and/or taste-masking agent may vary depending on the type of tablet and the intended recipients and the identity of the flavouring and/or taste-masking agent.

The amount of coating deposited on the tablet is typically in the range of from about 1.0% to about 6.0% weight gain, preferably from 2.0% to 4.0% weight gain, which means the weight gain of the tablet upon coating relative to the weight of the uncoated tablet.

In the case of orally administrable, rapidly disintegrating dosage forms, disintegration takes place immediately upon administration allowing to quickly release the active agent or forming small particles containing the active agent in the oral cavity. Suitable disintegration rates range from 1 second to 3 minutes. A preferred disintegration time is typically less than 30 seconds, measured according to standard European Pharmacopeia testing method.

Thus in one embodiment, the formulation is a tablet made by standard tabletting techniques, such as direct compression, and dry granulation, comprising iron oxy-hydroxide, a stabilization agent, an excipient (different from the stabilization agent), including, in particular, one or more sweeteners, taste-enhancing agents, flavouring agents, superdisintegrants, glidants, antioxidants and the like. Wet processing techniques must be avoided. This is due to the fact that in case of using organic solvents, typically isopropanol, solvent remains in the granulate after drying which might not be compatible with the product specification. In case of using water as a solvent for wet granulation, iron release from the product is increased which should be avoided under any circumstances for the inventive phosphate adsorber compositions. Extrusion techniques may cause problems in that, when using high loadings of iron, small hard balls are formed which are not suitable for the invention since they hardly show any phosphate adsorbing properties.

In dry granulation, powdered components are typically mixed prior to being compacted, also called pre-compression, to yield hard slugs which are then ground and sieved before the addition of other ingredients and final compression.

Preferably, the compositions of the invention are made by direct compression, which may be considered to be the simplest and the most economical process for producing tablets.

In a preferred embodiment of the invention the compositions of the invention are made by mixing most of the ingredients (more than 50%, preferably more than 70%, and more preferably more than 90% up to 100% of the total weight of the ingredients), for example those of the ingredients presented in table 1, in the form of an aqueous suspension (amount of dry substance, for example, 1 to 50% (w/w), preferably 10 to 40% (w/w), more preferably 20 to 30% (w/w)), subjecting said suspension to known spray-drying processes under conventional conditions of exposure to hot gases such as air or preferably nitrogen to temperatures of from 135° C. to 200° C. to obtain a flowable powder, which is optionally subsequently mixed with additional ingredients (e.g. as shown in Table 2) and subsequently directly compressed under a range of compression forces such as from 10 to 20 kN to obtain a tablet.

Preferably, the suspension contains 3 to 9% (w/w) of iron, more preferably 4 to 8% (w/w), most preferably 6% (w/w).

Care has to be taken that the diameter and the height of the spray drying column are sufficiently large. Further, the temperature has to be chosen in a range that the excipients and other ingredients neither melt nor caramelize. Both of these processed do not lead to a dry powder but to a solid melt, which is unsuitable for the present invention.

Preferably, the flowable powder, before tabletting, is first compacted using dry compacting in order to reduce the amount of fine powder (dust) and to homogenize the particle size. In doing this a hardness of the obtained tablets in the range of 25 to 400 N is achieved. The compression force is adjusted in a range that the hardness of the tablets obtained from the compacted mixture is 50 to 100 N for chewable tablets, and 100 to 200 N in case of coated tablets or swallowing tablets. If these ranges are used, the disintegration time of the obtained tablets is within the specification required by Ph. Eur.

It has been found surprisingly that, in particular, due to this method the amount of excipients required to obtain tablets with suitable properties, for example in respect to tablet strength, disintegration behaviour etc. can be reduced, whereby pharmaceutical compositions, in particular, in tablet form can be produced having a high load of iron oxy hydroxide.

It is understood that the exact amounts of ingredients will determine the size and depth of the tablet. Tablets capable of rapid disintegration (either in the oral cavity, i.e. chewing tablets, or in a small amount of liquid prior to ingestion) can have any geometrical shape, such as round, square, triangular, etc. Typically they are round and have preferably a diameter of 15 to 30 mm, most preferably 20 mm and a height of 2 to 8 mm, preferably 4 to 6 mm. Film coated tablets for intact swallowing are typically in oblong form, for example about 19 mm in length, 10 mm in width and 8 mm in height. These examples are merely illustrative and by no means limiting. A person skilled in the art will know to choose the appropriate forms depending on the amount of total ingredients. Compression should be sufficient to hold the ingredients together during dose administration, while allowing easy disintegration in the oral cavity. Typically 10 to 20 kN are used.

In another embodiment, the pharmaceutical composition is in form of granules suitable for disintegration in the oral cavity or rapid dissolution in small amounts of water. The granules may be prepared by high shear granulation or preferably fluidized bed granulation or (dry) mixing processes. As pointed out above, wet techniques using solvents must be avoided. The granules may be filled in capsules or sachets for storage and administration to the oral cavity.

In a further embodiment, as an alternative to spry-drying, the pharmaceutical composition can be provided in form of a wafer. The wafer may be formed by compressing a powder, lyophilizing a cake, or evaporating a suspension, emulsion or gel. Alternatively, the mixed dry materials could be flattened or compressed in a compression machine or between rollers to form the powder e.g. into a sheet that may be cut to an appropriate size that can be inserted in the oral cavity. In one embodiment, the wafer is formed by suspending the active agent, solvent, binding agent or other additives in a solvent such as water. A predetermined amount of the suspension is placed in wells in a plastic mold and lyophilized in the wells to remove the water and form a wafer.

As mentioned hereinabove, the compositions of the invention are indicated for use in the known indications of essentially non-bioabsorbable iron oxy-hydroxide, particularly for the selective removal of inorganic phosphate such as in the treatment of hyperphosphataemia.

Therefore, in a further aspect the invention provides a composition of the invention for use in the treatment of hyperphosphataemia.

In another aspect the invention provides a method for treating hyperphosphataemia comprising administering a composition of the invention to a patient in need thereof.

In yet another aspect the invention provides the use of a composition of the invention in the preparation of a medicament for the treatment of hyperphosphataemia.

The utility of the compositions of the invention may be observed in standard clinical tests.

The exact amount of iron oxy-hydroxide and composition to be administered depends on several factors, for example the severity of the illness, the desired duration of treatment and the like.

The invention is explained in more detail by means of the following specific, non-limiting examples:

EXAMPLES

Direct compression was performed using a standard tabletting press at a compression force of 10 to 20 kN. Spraydrying processes were performed at a temperature of 135 to 200° C.

Tablet Test Methods:

Tablet hardness and disintegration time was determined according to standard European Pharmacopeia testing methods.

Example 1: Preparation of Stabilized Iron Oxy-Hydroxide Premixture

A stabilized iron oxy-hydroxide premixture was prepared by mixing amounts/ratios of an iron oxy-hydroxide suspension (prepared according to EP 0 868 125 B1) with the excipients according to Table 1. This suspension was subjected to spray-drying at 135 to 200° C. to obtain a premixture in form of a flowable powder. This premixture was subjected to direct compression to obtain a tablet, the composition of which is shown in Table 1.

TABLE 1

| Component | Ex. 1a mg | Ex. 1b mg | Ex. 1c mg | Ex. 1d mg | Ex. 1e mg |
|---|---|---|---|---|---|
| Fe—OOH | 800 | 800 | 800 | 800 | 800 |
| Saccharose[1)] | 800 | 800 | 800 | 800 | — |
| Native starch[2)] | — | 533 | 400 | 533 | — |
| Pregelatinised starch[3)] | 800 | 267 | 400 | 267 | — |
| Polyplasdone ® XL[4)] | — | — | — | 120 | — |
| Dextrin[2)] | — | — | — | — | 1600 |
| Water[5)] | 8400 | 8400 | 8400 | 8400 | 8400 |
| Disintegration time (seconds) | nd | nd | nd | 35 | nd |

[1)]stabilizer
[2)]filler/disintegrant
[3)]stabilizer/binder/filler/disintegrant
[4)]superdisintegrant
[5)]water is not present anymore in the premixture after drying, except a remaining portion of approx. 5% of the dry weight (total of other components)

Example 2: Preparation of Tablets

A dry mixture was prepared by mixing the ingredients according to table 2 and subjected to direct compression to obtain a tablet.

TABLE 2

| component | Ex. 2a mg | Ex. 2b mg | Ex. 2c mg | Ex. 2d mg |
|---|---|---|---|---|
| Premixture (according to Example 1a-d) | 2500 (1a) | 2500 (1b) | 2500 (1c) | 2500 (1d) |
| Flavour of choice | 15 | 15 | 15 | 15 |
| NHDC | 0.025 | 0.025 | 0.025 | 0.025 |
| Aerosil ® | 25 | 25 | 25 | 25 |
| Mg-stearate | 12.5 | 12.5 | 12.5 | 12.5 |
| Explotab ® | — | 12.5 | 200 | — |
| Polyplasdone ® XL | — | — | — | 50 |

Example 3: Film-Coating of Tablets

Tablets obtained according to Example 2, but with only 50% of the amounts, were compressed into oblong form and subsequently film-coated (weight gain from 2 to 5%) by mixing the ingredients according to the following table:

TABLE 3

| component | mg |
|---|---|
| Opadry ® II White | 83.4 |
| Optaflow ® WA | 1.7 |
| Apricot aroma | 1.7 |

Example 4: Granules

The powder obtained according to Example 1 e was wet granulated using high shear granulation with isopropanol as granulating liquid by adding the ingredients according to the following table:

TABLE 4

| component | mg |
|---|---|
| Premixture (Ex. 1e) | 2500 |
| Neosorb ® (Sorbitol) | 1060 |
| Polyvinylpyrrolidon | 200 |
| Xanthan | 37.5 |

Example 5: Preparation of a Final Instantly Dispersable Granulate for Filling into Sachets or Stickpacks A dry mixture was prepared by mixing the ingredients according to the following table and subjected to subsequent filling into sachets or stickpacks.

TABLE 5

| Component | mg |
|---|---|
| Granules (Ex. 4, variants obtained from different base materials) | 3797.5 |
| Aspartam | 15 |
| Flavour* | 70 |
| citric acid | 155 |

*"refreshing flavour" such as cola, verveine, blackberry

Example 6: Preparation of a Final Instantly Dispersable Granulate for Filling into Sachets or Stickpacks A dry mixture was prepared by mixing the ingredients according to the following table and subjected to subsequent filling into sachets or stickpacks:

TABLE 6

| Component | mg |
|---|---|
| Granules (Ex. 4, variants obtained from different base materials | 3797.5 |
| Aspartam | 25 |
| Caramel aroma | 100 |
| Vanilla aroma | 30 |

Example 7: Preparation of Flowable Powders 9.6 kg FeOOH (corresponding to 6.0 kg Fe) was suspended in water together with the amounts of excipients and adjuvants shown in Table 7. 100 kg of the suspension was subjected to spray-drying. The iron loading of the obtained powders is given in Table 8.

TABLE 7

| Product | Amount of FeOOH [kg] | Sucrose [kg] | PST[1] [kg] | Dextrin [kg] | Lycatab ®[2] [kg] |
|---|---|---|---|---|---|
| a | 9.6 | 8.9 | 5.9 | | 3.0 |
| b | 9.6 | 6.9 | | | |
| c | 9.6 | | | 6.9 | |
| d | 9.6 | 2.0 | 2.0 | 2.9 | |
| e | 9.6 | 1.7 | 1.7 | 1.7 | 1.7 |
| f | 9.6 | 3.0 | 2.1 | 0.9 | 0.9 |
| g | 9.6 | 3.4 | 2.3 | | 1.1 |

[1]potato starch
[2]pregelatinised starch, available from Roquette

TABLE 8

| Product | Fe [% w/w] | FeOOH (Fe × 1.6) [% w/w] | LOD[1] (approx.) [% w/w] | Total amount of product [kg] |
|---|---|---|---|---|
| a | 20-22 | 33.6 | 4 | 28.6 |
| b | 34-36 | 56 | 4 | 17.1 |
| c | 34-36 | 56 | 4 | 17.1 |
| d | 34-36 | 56 | 4 | 17.1 |
| e | 34-36 | 56 | 4 | 17.1 |
| f | 34-36 | 56 | 4 | 17.1 |
| g | 34-36 | 56 | 4 | 17.1 |

[1]Loss on drying, determined by a halogen moisture analyzer (constant mass; change in mass not more than 1 mg per 180 seconds).

Example 8: Tabletting of the Obtained Flowable Powders

The product obtained in Examples 7a) to g) were mixed with the ingredients shown in Table 9a, and tablets were formed of the obtained mixtures. The Fe content, Fe release at pH 3 and phosphate adsorption of the obtained tablets are given in Table 9b.

The Fe release was measured according to European Pharmacopeia chapter 2.9.3 using standard dissolution equipment and parameters as described in the monograph. The test medium was water, pH 3 was adjusted using hydrochloric acid. Samples were taken after 2 h and iron content analyzed by titration.

Phosphate adsoprtion was measured as described in WO 2006/000547 by dissolving the obtained tablet in a defined amount of phosphate solution of a specific concentration, adjusting the pH to 3, reacting for 2 hours at 37° C., centrifugation, decanting and measuring the phosphate content via ionic chromatography or photometric determination.

TABLE 9a

| Component | Amount [% w/w] |
|---|---|
| Flowable powder 7a)-7g) | 98-93, without coating 98 to 95% |
| Aroma including taste masking agent (neohesperidine dihydrochalcone) | 0.2-1 |
| Lubricant/glidant/flow aid | total 0.5-2 |
| Compression aid (ProSolv ®) | 0.5-2 |
| Optionally coating | max. 3 |

TABLE 9b

| product | Flowable powder used | Fe loading [% w/w] | Fe release at pH 3 [% w/w] | Phosphate absorption [mg P/mg Fe] |
|---|---|---|---|---|
| 8a | 7a | 19.5 | 1.8 | 0.314 |
| 8b | 7b | 34.7 | 3.4 | 0.319 |
| 8c | 7c | 36.7 | 0.5 | 0.241 |
| 8d | 7d | 35.9 | 0.4 | 0.216 |
| 8e | 7e | 36.3 | 0.6 | 0.229 |
| 8f | 7f | 36.2 | 0.2 | 0.219 |
| 8g | 7g | 37.5 | 0.2 | 0.170 |

The invention claimed is:

1. A pharmaceutical composition comprising iron oxy-hydroxide, saccharose, native starch, and pregelatinized starch,
wherein the iron oxy-hydroxide is present in an amount of 10 to 80% (w/w) expressed in relation to the total weight of the composition,
wherein the pharmaceutical composition is in a form of a chewable tablet for oral administration, and
wherein the amount of iron oxy-hydroxide per dosage form is 700 mg to 1700 mg.

2. The pharmaceutical composition according to claim 1 wherein the iron oxy-hydroxide is stabilized by at least saccharose, native starch, and/or pregelatinized starch.

3. The pharmaceutical composition according to claim 1 having an iron release rate of below 2.5% w/w.

4. The pharmaceutical composition according to claim 1, wherein the iron oxy-hydroxide is essentially non-bioabsorbable.

5. The pharmaceutical composition according to claim 1 further comprising at least one additional component chosen from flavouring agents, sweeteners, taste-enhancing agents, and coloring agents, and
optionally at least one excipient chosen from superdisintegrants, glidants, and antioxidants.

6. The pharmaceutical composition according to claim 5,
wherein the sweeteners, if present, is/are present in an amount of 0.01 to 2.5% (w/w),
wherein the taste-enhancing agents, if present, is/are present in an amount of 0.1 to 50 ppm,
wherein the flavouring agents, if present, is/are present in an amount of 0.01 to 10% (w/w),
wherein the superdisintegrants, if present, is/are present in an amount of 0.1 to 10% (w/w), and/or
wherein the glidants, if present, is/are present in an amount of 0.01 to 10% (w/w), each expressed in relation to the total weight of the composition.

7. The pharmaceutical composition according to claim 1, wherein native starch and pregelatinized starch are present in a ratio (native:pregelatinized) in the range of 10:1 to 0.5:1.

8. The pharmaceutical composition according to claim 1, wherein native starch and pregelatinized starch are present in a ratio (native:pregelatinized) in the range of 3:1 to 0.5:1.

9. The pharmaceutical composition according to claim 8 wherein the iron oxy-hydroxide is stabilized by at least saccharose, native starch, and/or pregelatinized starch.

10. The pharmaceutical composition according to claim 1, wherein native starch and pregelatinized starch are present in a ratio (native:pregelatinized) in the range of 2:1 to 1:1.

11. The pharmaceutical composition according to claim 1, wherein the iron oxy-hydroxide is present in an amount of 30 to 65% (w/w) expressed in relation to the total weight of the composition.

12. The pharmaceutical composition according to claim 11, wherein native starch and pregelatinized starch are present in a ratio (native:pregelatinized) in the range of 10:1 to 0.5:1.

13. The pharmaceutical composition according to claim 11, wherein native starch and pregelatinized starch are present in a ratio (native:pregelatinized) in the range of 3:1 to 0.5:1.

14. The pharmaceutical composition according to claim 11, wherein native starch and pregelatinized starch are present in a ratio (native:pregelatinized) in the range of 2:1 to 1:1.

15. The pharmaceutical composition according to claim 1, wherein the iron oxy-hydroxide is present in an amount of about 30 to about 35% (w/w) expressed in relation to the total weight of the composition.

16. The pharmaceutical composition according to claim 15, wherein the iron oxy-hydroxide comprises beta iron oxy-hydroxide.

17. The pharmaceutical composition according to claim 15, wherein native starch and pregelatinized starch are present in a ratio (native:pregelatinized) in the range of 10:1 to 0.5:1.

18. The pharmaceutical composition according to claim 15, wherein native starch and pregelatinized starch are present in a ratio (native:pregelatinized) in the range of 3:1 to 0.5:1.

19. The pharmaceutical composition according to claim 15, wherein native starch and pregelatinized starch are present in a ratio (native:pregelatinized) in the range of 2:1 to 1:1.

20. The pharmaceutical composition according to claim 1, wherein the iron oxy-hydroxide is present in an amount of about 27 to about 35% (w/w) expressed in relation to the total weight of the composition.

21. The pharmaceutical composition according to claim 20, wherein the iron oxy-hydroxide comprises beta iron oxy-hydroxide.

22. The pharmaceutical composition according to claim 20, wherein native starch and pregelatinized starch are present in a ratio (native:pregelatinized) in the range of 10:1 to 0.5:1.

23. The pharmaceutical composition according to claim 20, wherein native starch and pregelatinized starch are present in a ratio (native:pregelatinized) in the range of 3:1 to 0.5:1.

24. The pharmaceutical composition according to claim 20, wherein native starch and pregelatinized starch are present in a ratio (native:pregelatinized) in the range of 2:1 to 1:1.

25. The pharmaceutical composition according to claim 1, wherein the iron oxy-hydroxide is present in an amount of about 29 to about 32% (w/w) expressed in relation to the total weight of the composition.

26. The pharmaceutical composition according to claim 25, wherein the iron oxy-hydroxide comprises beta iron oxy-hydroxide.

27. The pharmaceutical composition according to claim 25 further comprising
at least one additional component chosen from flavouring agents, sweeteners, taste-enhancing agents, and coloring agents, and
optionally at least one excipient chosen from superdisintegrants, glidants, and antioxidants.

28. The pharmaceutical composition according to claim 27, wherein the sweeteners, if present, is/are present in an amount of 0.01 to 2.5% (w/w), wherein the taste-enhancing agents, if present, is/are present in an amount of 0.1 to 50 ppm, wherein the flavouring agents, if present, is/are present in an amount of 0.01 to 10% (w/w), wherein the superdisintegrants, if present, is/are present in an amount of 0.1 to 10% (w/w), and/or wherein the glidants, if present, is/are present in an amount of 0.01 to 10% (w/w), each expressed in relation to the total weight of the composition.

29. The pharmaceutical composition according to claim 25, wherein native starch and pregelatinized starch are present in a ratio (native:pregelatinized) in the range of 10:1 to 0.5:1.

30. The pharmaceutical composition according to claim 25, wherein native starch and pregelatinized starch are present in a ratio (native:pregelatinized) in the range of 3:1 to 0.5:1.

31. The pharmaceutical composition according to claim 30 wherein the iron oxy-hydroxide is stabilized by at least saccharose, native starch, and/or pregelatinized starch.

32. The pharmaceutical composition according to claim 30 further comprising at least one additional component chosen from flavouring agents, sweeteners, taste-enhancing agents, and coloring agents, and optionally at least one excipient chosen from superdisintegrants, glidants, and antioxidants.

33. The pharmaceutical composition according to claim 32, wherein the sweeteners, if present, is/are present in an amount of 0.01 to 2.5% (w/w), wherein the taste-enhancing agents, if present, is/are present in an amount of 0.1 to 50 ppm, wherein the flavouring agents, if present, is/are present in an amount of 0.01 to 10% (w/w), wherein the superdisintegrants, if present, is/are present in an amount of 0.1 to 10% (w/w), and/or wherein the glidants, if present, is/are present in an amount of 0.01 to 10% (w/w), each expressed in relation to the total weight of the composition.

34. The pharmaceutical composition according to claim 25, wherein native starch and pregelatinized starch are present in a ratio (native:pregelatinized) in the range of 2:1 to 1:1.

35. The pharmaceutical composition according to claim 1, wherein the iron oxy-hydroxide is present in an amount of about 27 to about 32% (w/w) expressed in relation to the total weight of the composition.

36. The pharmaceutical composition according to claim 35, wherein the iron oxy-hydroxide comprises beta iron oxy-hydroxide.

37. The pharmaceutical composition according to claim 35, wherein native starch and pregelatinized starch are present in a ratio (native:pregelatinized) in the range of 10:1 to 0.5:1.

38. The pharmaceutical composition according to claim 35, wherein native starch and pregelatinized starch are present in a ratio (native:pregelatinized) in the range of 3:1 to 0.5:1.

39. The pharmaceutical composition according to claim 35, wherein native starch and pregelatinized starch are present in a ratio (native:pregelatinized) in the range of 2:1 to 1:1.

40. A pharmaceutical composition comprising iron oxy-hydroxide, saccharose, and starch, wherein the iron oxy-hydroxide is present in an amount of 10 to 80% (w/w) expressed in relation to the total weight of the composition, wherein the pharmaceutical composition is in a form of a chewable tablet, and wherein the amount of iron oxy-hydroxide per tablet is about 800 mg.

41. The pharmaceutical composition according to claim 40, wherein the iron oxy-hydroxide is stabilized by at least saccharose and/or starch.

42. The pharmaceutical composition according to claim 40 having an iron release rate of below 2.5% w/w.

43. The pharmaceutical composition according to claim 40, wherein the iron oxy-hydroxide is essentially non-bioabsorbable.

44. The pharmaceutical composition according to claim 40 further comprising at least one additional component chosen from flavouring agents, sweeteners, taste-enhancing agents, and coloring agents, and optionally at least one excipient chosen from superdisintegrants, glidants, and antioxidants.

45. The pharmaceutical composition according to claim 44, wherein the sweeteners, if present, is/are present in an amount of 0.01 to 2.5% (w/w), wherein the taste-enhancing agents, if present, is/are present in an amount of 0.1 to 50 ppm, wherein the flavouring agents, if present, is/are present in an amount of 0.01 to 10% (w/w), wherein the superdisintegrants, if present, is/are present in an amount of 0.1 to 10% (w/w), and/or wherein the glidants, if present, is/are present in an amount of 0.01 to 10% (w/w), each expressed in relation to the total weight of the composition.

46. The pharmaceutical composition according to claim 40, wherein the iron oxy-hydroxide is present in an amount of 30 to 65% (w/w) expressed in relation to the total weight of the composition.

47. The pharmaceutical composition according to claim 40, wherein the iron oxy-hydroxide is present in an amount of about 30 to about 35% (w/w) expressed in relation to the total weight of the composition.

48. The pharmaceutical composition according to claim 40, wherein the iron oxy-hydroxide is present in an amount of about 27 to about 35% (w/w) expressed in relation to the total weight of the composition.

49. The pharmaceutical composition according to claim 48, wherein the iron oxy-hydroxide comprises beta iron oxy-hydroxide.

50. The pharmaceutical composition according to claim 40, wherein the iron oxy-hydroxide is present in an amount of about 29 to about 32% (w/w) expressed in relation to the total weight of the composition.

51. The pharmaceutical composition according to claim 50 further comprising at least one additional component chosen from flavouring agents, sweeteners, taste-enhancing agents, and coloring agents, and optionally at least one excipient chosen from superdisintegrants, glidants, and antioxidants.

52. The pharmaceutical composition according to claim 51, wherein the sweeteners, if present, is/are present in an amount of 0.01 to 2.5% (w/w), wherein the taste-enhancing agents, if present, is/are present in an amount of 0.1 to 50 ppm, wherein the flavouring agents, if present, is/are present in an amount of 0.01 to 10% (w/w), wherein the superdisintegrants, if present, is/are present in an amount of 0.1 to 10% (w/w), and/or wherein the glidants, if present, is/are present in an amount of 0.01 to 10% (w/w), each expressed in relation to the total weight of the composition.

53. The pharmaceutical composition according to claim 50, wherein the iron oxy-hydroxide is stabilized by at least saccharose and/or starch.

54. The pharmaceutical composition according to claim 40, wherein the iron oxy-hydroxide is present in an amount of about 27 to about 32% (w/w) expressed in relation to the total weight of the composition.

55. The pharmaceutical composition according to claim 54 further comprising at least one additional component chosen from flavouring agents, sweeteners, taste-enhancing agents, and coloring agents, and optionally at least one excipient chosen from superdisintegrants, glidants, and antioxidants.

56. The pharmaceutical composition according to claim 55, wherein the sweeteners, if present, is/are present in an amount of 0.01 to 2.5% (w/w), wherein the taste-enhancing agents, if present, is/are present in an amount of 0.1 to 50 ppm, wherein the flavouring agents, if present, is/are present in an amount of 0.01 to 10% (w/w), wherein the superdisintegrants, if present, is/are present in an amount of 0.1 to 10% (w/w), and/or wherein the glidants, if present, is/are present in an amount of 0.01 to 10% (w/w), each expressed in relation to the total weight of the composition.

57. The pharmaceutical composition according to claim 54, wherein the iron oxy-hydroxide is stabilized by at least saccharose and/or starch.

58. The pharmaceutical composition according to claim 1 or 40, further comprising at least one glidant chosen from magnesium stearate and silica derivatives, wherein said silica derivatives are chosen from colloidal silica, pyrogenic silica, hydrated sodium silicoaluminate, colloidal silicon dioxide, and talcum.

59. The pharmaceutical composition according to claim 58, wherein the glidants is/are present in an amount of 0.1 to 5% (w/w) expressed in relation to the total weight of the composition.

60. The pharmaceutical composition according to claim 59, wherein the iron oxy-hydroxide is stabilized by at least saccharose and/or starch.

61. The pharmaceutical composition according to claim 59, wherein the glidants is/are present in an amount of 1 to 2% (w/w) expressed in relation to the total weight of the composition.

62. The pharmaceutical composition according to claim 1 or 40, further comprising at least one superdisintegrant chosen from cross-linked polyvinylpyrrolidones, modified starches, and modified cellulose.

63. The pharmaceutical composition according to claim 62, wherein the superdisintegrants is/are present in an amount of 0.5 to 8% (w/w) expressed in relation to the total weight of the composition.

64. The pharmaceutical composition according to claim 63, wherein the iron oxy-hydroxide is stabilized by at least saccharose and/or starch.

65. The pharmaceutical composition according to claim 62, further comprising at least one glidant chosen from magnesium stearate and silica derivatives, wherein said silica derivatives are chosen from colloidal silica, pyrogenic silica, hydrated sodium silicoaluminate, colloidal silicon dioxide, and talcum.

* * * * *